US007258987B2

(12) United States Patent
LaMorte et al.

(10) Patent No.: US 7,258,987 B2
(45) Date of Patent: Aug. 21, 2007

(54) METHODS OF CYTODIAGNOSTIC STAGING OF NEOPLASIA AND SQUAMOUS CELL CARCINOMA

(75) Inventors: Vickie J. LaMorte, Tustin Ranch, CA (US); Melinda Szendefi, Brüttisellen (CH); Heinrich Walt, Zollikerberg (CH)

(73) Assignee: The Regents of the University of California, Oakland, CA (US)

( * ) Notice: Subject to any disclaimer, the term of this patent is extended or adjusted under 35 U.S.C. 154(b) by 768 days.

(21) Appl. No.: 10/251,887

(22) Filed: Sep. 23, 2002

(65) Prior Publication Data

US 2003/0092047 A1 May 15, 2003

Related U.S. Application Data

(60) Provisional application No. 06/324,108, filed on Sep. 21, 2001.

(51) Int. Cl.
*G01N 33/53* (2006.01)
(52) U.S. Cl. .......................... 435/7.1; 435/6; 435/7.23; 530/350
(58) Field of Classification Search ................. 424/9.1, 424/573, 155.1; 435/40.52; 436/501
See application file for complete search history.

(56) References Cited

OTHER PUBLICATIONS

Kamitani T. et al. Journal of Biological Chemistry 273(41): 26675-26682, 1998.*
Muller S. et al. The EMBO Journal 17(1): 61-70, 1998.*
Ahn, JH, et al. (1998) "Disruption of PML subnuclear domains by the acidic IE1 protein of human cytomegalovirus is mediated through interaction with PML and may modulate a RING finger-dependent cryptic transactivator function of PML" Mol. Cell Bio. 18:4899-4913.
Ahn, JH, et al. (1999) "The human cytomegalovirus IE2 and UL112-113 proteins accumulate in viral DNA replication compartments that initiate from the periphery of promyelocytic leukemia protein-associated nuclear bodies (PODS or ND10)" J. Virol. 73:10458-10471.
Borrow, J., et al. (1990) "Molecular analysis of acute promyelocytic leukemia breakpoint cluster region on chromosome 17" Science 249:1577-1580.
Brisson, J., et al (1994) "Risk factors for cervical intraepithelial neoplasia differences between low-and high-grade lesions" American Journal Epidemiology 140:700-710.
"Preinvasive disease of the cervix, vagina and vulva", Clinical Gynecolgic Oncology, 4th Ed., (1993) Di Saia, P.J. and Creasman, WT, eds. Mosby Year Book, pp. 1-47.
Doucas, V, et al (1993) "The PML-retinoic acid receptor α translocation converts the receptor from an inhibitor to a retinoic acid-dependent activator of transcription factor AP-1" PNAS USA 90:9345-9349.
Duprez, E, et al. (1999) "SUMO-1 modification of the acute promyelocytic leukaemia protein PML: implications for nuclear localization" J. Cell Sci. 112:381-393.
Dyck, J. et al. (1994) "A novel macromolecular structure is a target of the promyelocyte-retinoic acid receptor oncoprotein" Cell 76:333-343.
Everett, R.D. et al. (1994) "HSV-1 IE protein Vmw110 causes redistribution of PML" EMBO J. 13:5062-5069.
Gambacorta, M, et al. (1996) "Heterogeneous nuclear expression of the promyelocytic leukemia (PML) protein in normal and neoplastic human tissues" Am. J. Path. 149:2023-2035.
Goddard, AD, et al. (1991) "Characterization of a zinc finger gene disrupted by the T (15; 17) in acute promyelocytic leukemia" Science 254:1371-1374.
Gostissa, M, et al. (1999) "Activation of $p^{53}$ by conjugation to the eubiquitin-like protein SUMO-1" EMBO J 18:6462-6471.
He, Dalin et al. (1997) "Adenovirus-mediated expression of PML suppresses growth and tumorigenicity of prostate cancer cells" Cancer Res. 57:1868-1872.
Hodges, M, et al. (1998) "Protein regulation: tag wrestling with relatives of ubiquitin" Current Biol. 8:749-752.
Hugues de Thé, et al. (1990) "The t (15;17) Translocation of Acute Promyelocytic leukaemia fuses the retinoic acid receptor gene to a novel transcribed locus" Nature 347:558-561.
Hughes de Thé, et al. (1991) "The PML-RARα Fusion mRNA generated by the t(15;17) translocation in acute promyelocytic leukemia encodes a functionality altered RAR" Cell 66:675-684.
Ishov, AM, et al. (1999) "PML Is Critical for ND10 formation and recruits the PML-interacting protein daxx to this nuclear structure when modified by SUMO-1" J Cell Biol. 147:221-233.
Kakizuka, A. et al. (1991) "Chromosomal Translocation t(15;17) in Human Acute Promyelocytic Leukemia Fuses RARα with a Novel Putative Transcription Factor, PML" Cell 66:663-674.
Klaes, R. et al. (2001) "Overexpression of $p16^{INK4A}$ as a Specific Marker for Dysplastic and Neoplastic Epithelial Cells of the Cervice Uteri" Int. J Cancer 92:276-284.

(Continued)

*Primary Examiner*—Larry R. Helms
*Assistant Examiner*—David Humphrey
(74) *Attorney, Agent, or Firm*—Suzannah K. Sundby, Esq.; Smith, Gambrell & Russell, LLP

(57) ABSTRACT

Methods of diagnosing whether an epithelial tissue is an abnormal tissue by determining an expression pattern for PML in the epithelial tissue; determining an expression pattern for nuclear bodies in the epithelial tissue; determining SUMO-1 colocalization and comparing the expression pattern for PML and the expression pattern for nuclear bodies with a control are disclosed. Also disclosed are methods for diagnosing whether a subject has mild dysplasia, moderate dysplasia, Type A severe dysplasia, Type B severe dysplasia, cervical squamous cell carcinoma, or poorly-differentiated cervical squamous cell carcinoma, by determining an expression pattern for PML, an expression pattern for nuclear bodies, and SUMO-1 colocalization and determining whether the sample is consistent with expression patterns expected for mild dysplasia, moderate dysplasia, Type A severe dysplasia, Type B severe dysplasia, cervical squamous cell carcinoma, or poorly-differentiated cervical squamous cell carcinoma.

31 Claims, 4 Drawing Sheets
(3 of 4 Drawing Sheet(s) Filed in Color)

OTHER PUBLICATIONS

Koken MHM, et al. (1994) "The t(15;17) Translocation Alters a Nuclear Body in a Retinoic Acid-Reversible Fashion" EMBO J 13(5):1073-7083.

Koken MHM, et al. (1995) "The PML Growth-Suppressor has an Altered Expression in Human Oncogenesis" Oncogene 10:1315-1324.

Kretz-Remy, C, et al. (1999) "SUMO/sentrin: protein modifiers regulating important cellular functions" Cell Biol. 77:299-309.

Lavau, C, et al. (1995) "The acute promyelocytic leukaemia-associated PML gene is induced by interferon" Oncogene 11:871-876.

Le, XF et al. (1996) "Analysis of the growth and transformation suppressor domains of promyelocytic leukemia gene, PML" J Biol. Chem. 274:130-135.

Le, XF et al. (1998) "Recombinant PML adenovirus suppresses growth and tumorigenicity of human breast cancer cells by inducing G1 cell cycle arrest and apoptosis" Oncogene 16:1839-1849.

Lin, R.J. (1999) "Molecular genetics of acute promyelocytic leukemia" Trends in Genetics 15:179-183.

Litvinov, SV, et al. (1996) "Expression of ep-cam in cervical squamous epithelia correlates with an increased proliferation and the disappearance of markers for terminal differentiation" Am. J Path 148:865-875.

Longo, L. et al (1990) "Rearrangements and aberrant expression of the retinoic acid receptor gene in acute promyelocytic leukemias" J Exp. Med. 172:1571-1575.

Lowy, DR et al. (1994) "Genital human papillomavirus infection" Proc. Natl. Acad. USA 19:2436-2440.

Maul, G.G, et al. (1993) "Modification of discrete nuclear domains induced by herpes simplex virus type 1 immediate early gene 1 product (ICP0)" J Gen. Virology, 74:2679:2690.

Maul, Gerd G, et al. (1994) "The nuclear location of PML, a cellular member of the $C_3HC_4$ viral protein ICP0" J Gen. Virology 75:1223-1233.

Maul, Gerd G, et al. (1995) "Nuclear domain 10 (ND10) associated proteins are also present in nuclear bodies and redistribute to hundreds of nuclear sites after stress" J Cell. Biochem. 59:498-513.

Mu et al. (1994) "Growth suppressor function of PML in APL", Molecular and Cellular Biology 14:6859-6867.

Mueller, S, et al. (1999) "Viral immediate-early proteins abrogate the modification by SUMO-1 of PML and Sp100 proteins, correlating with nuclear body disruption" J Virology 73:5137-5143.

Pandolfi, PP, et al. (1991) "Structure and origin of the acute promyelocytic leukemia myl/RARα cDNA and characterization of its Retinoid-binding and transactivation properties" Oncogene 6:1285-1292.

Rodriguez, MS, et al. (1999) "SUMO-1 modification activates the transcriptional response of $_p53$" EMBO J 18:6455-6461.

Ruggero, MS et al. (2000) "The puzzling multiple lives of PML and its role in the genesis of cancer" BioEssays 22:827-835.

Saitoh, H, et al. (1998) "Ubc9p and the conjugation of SUMO-1 to RanGAP1 and RanBP2" Current Biology 8:121-124.

Physiological Alterations Within the Cervical Epithelium (1976) "The cervical epithelium during puberty and adolescence" by Singer, A. The Whitefriars Press Ltd. pp. 1-36.

Skyldbert, B, et al. (1999) "Laminin-5 as a marker of invasiveness in cervical lesions" J Natl. Cancer Inst. 91:1882-1887.

Sternsdorf, T, et al. (1997) "Evidence for covalent modification of the nuclear dot-associated proteins PML and Sp100 by PIC1/SUMO-1" J Cell Biol. 139(7):1621-1634.

Terris, B, et al. (1995) "PML nuclear bodies are general targets for inflammation and cell proliferation" Cancer Research 55:1590-1597.

Vassallo, J, et al. (2000) "High risk HPV and p53 protein expression in cervical intraepithelial neoplasia" Intl. J Gyn. & Ob. 71:45-48.

Weis, K, et al. (1994) "Retinoic acid regulates aberrant nuclear localization of PML-RARα in acute promyelocytic leukemia cells" Cell 76:345-356.

Zhong, S, et al. (2000) "Role of SUMO-1-modified PML in nuclear body formation" Blood 95:2748-2753.

Zur Hausen, H. (1991) "Human papillomaviruses in the pathogenesis of anogenital cancer" Virology 184:9-13.

Ishov et al., "PML Is Critical for ND10 Formation and Recruits the PML-Interacting Protein DAXX to this Nuclear Structure When Modified by SUMO-1", J. Cell Biol. Oct. 18, 1999, vol. 147, No. 2, pp. 221-233.

Muller et al., "Conjugation with the Ubiquitin-Related Modifier SUMO-1 Regulates the Partitioning of PML Within The Nucleus", The EMBO J. 1998, vol. 17, No. 1, pp. 61-70 (see the entire reference, in particular, pp. 61, 62 and 68.

Duprez et al., "SUMO-1 Modification of the Acute Promyelocytic Leukaemia Protein PML: Implications for Nuclear Localisation" J. Cell Sci. 1999, vol. 112, pp. 381-393, see in particular pp. 381-382, 391 and 392.

Kretz-Remy, et al., SUMO/Sentrin: Protein Modifiers Regulating Important Cellular Functions, Biochem. Cell Biol. 1999, vol. 77, pp. 299-309, see in particular pp. 305-306.

\* cited by examiner

METHODS OF CYTODIAGNOSTIC STAGING OF NEOPLASIA AND SQUAMOUS CELL CARCINOMA

CROSS REFERENCE TO RELATED APPLICATIONS

This application claims the benefit of U.S. Provisional Patent Application No. 60/324,108, filed 21 Sep. 2001, listing Vickie J. LaMorte, Melinda Szendefi, and Heinrich Walt as joint inventors, which is herein incorporated by reference in its entirety.

BACKGROUND OF THE INVENTION

1. Field of the Invention

The present invention generally relates to methods of detecting PML-containing NBs and proteins therein for cytodiagnostic staging of neoplasia and squamous cell carcinoma. Specifically, the present invention relates to methods of diagnosing the different stages of cervical neoplasia and squamous cell carcinoma.

2. Description of the Related Art

Cervical cancer is one of the leading causes of cancer-related death in women worldwide and is the leading cause of cancer-related death in women in developing countries. Worldwide, there are approximately 500,000 new cases per year of which 15–20,000 cervical cancers are diagnosed in the United States. Moreover, abnormalities of the precancerous disease of the cervix occur in an estimated 500,000 to 1,000,000 women each year in the United States.

Cervical squamous cell carcinomas originate from a multilayered cervical epithelium and develop progressively over the course of years. See DiSaia, P J and Creasman, W T (1993) CLINICAL GYNECOLOGIC ONCOLOGY, 4th ed. Mosby Year Book pp. 1–36; and Singer, A (1976) THE CERVIX London: The Whitefriars Press Ltd. pp. 87–104. The tissue goes through a spectrum of hyperplastic changes classified clinically as cervical intraepithelial neoplasia (CIN), ranging from CIN I (mild dysplasia), followed by CIN II (moderate dysplasia) to CIN III (severe dysplasia), where it may eventually result in invasive cervical cancer. The molecular mechanisms that regulate the induction and progression of cervical squamous cell carcinoma (SCC) remain an unsolved problem of great clinical relevance. The main risk factors for cervical cancer include human papilloma virus infection, multiple sexual partners, long-term cigarette smoking, immunosuppression, and the use of oral contraceptive. See Brisson, J, et al. (1994) America Journal Epidemiology 140:700–710; Lowy, D R, et al. (1994) PNAS USA 91:2436–2440; and Zur Hausen, H (1991) Virology 184:9–13.

The promyelocyte (PML) protein was identified first in the pathogenesis of acute promyelocytic leukemia (APL). See Lin, R J, et al. (1999) Trends In Genetics 15:179–183; and Ruggero D, et al. (2000) Bioessays 22:827–835. This type of leukemia is categorically characterized by a chromosomal translocation t(15;17), which fuses the PML gene to the retinoic acid receptor α (RARα). See de Thé, H, et al. (1990) Nature 347:558–561; Borrow, J, et al. (1990) Science 249:1577–1580; Longo, L, et al. (1990) J Exp Med 172: 571–575; Kakizuka, A, et al. (1991) Cell 66:663–674; de Thé, H, et al. (1991) Cell 66:675–684; Goddard, A D, et al. (1991) Science 254:1371–1374; Pandolfi, P P, et al. (1991) Oncogene 6:1285–1292; Weis, K, et al. (1994) Cell 76:345–356; and Ruggero, D, et al. (2000) Bioessays 22:827–835. In normal cells, PML is found in discrete nuclear structures known as nuclear bodies (NBs) or PML oncogenic domains (PODs). See Dyck, J A, et al. (1994) Cell 76:333–343; Koken, M H, et al. (1994) EMBO J. 13:1073–1083; and Weis, K, et al. Cell 76:345–356. In APL cells, PML is displaced and presents in a microspeckled pattern. This altered pattern is thought to cause the disruption of the normal function of PML. See Lin, R J, et al. (1999) Trends In Genetics 15:179–183.

While a host of studies exist in the literature, a defined function has yet to be assigned to PML and its corresponding nuclear body. See Ruggero, D, et al. (2000) Bioessays 22:827–835. Studies on the biologic function of PML demonstrate that PML acts in a variety of cellular processes including apoptosis, cell cycle progression, and transcriptional regulation. See Mu, Z M, et al. (1994) Molecular and Cellular Biology 14:6858–6867; Le, X F et al. (1996) J. Biol. Chem. 271:130–135; He, D, et al. (1997) Cancer Res. 57:1868–1872; Le, X F, et al. (1998) Oncogene 16:1839–1849; Mu, Z M, et al. (1997) Carcinogenesis 18:2063–2069; Doucas, V, et al. (1993) PNAS USA 90:9345–9349; and Vallian, S, et al. (1998) Oncogene 16:2843–2853.

PML expression is modulated by multiple stimuli including viral infection, γ-irradiation, estrogen, and interferon. See Ruggero, D, et al. (2000) Bioessays 22:827–835; Maul, G G, et al. (1993) J. Gen. Virol. 74:2679–2690; Maul, G G, et al. (1994) J. Gen. Virol. 75:1223–1233; Lavau, C, et al. (1995) Oncogene 11:871–876; Mueller, S and Dejean, A (1999) J. Virology 73:5137–5143.

PML is overexpressed in distinct pathological situations that are associated with stimulated transcription and cell hyperactivity, such as in inflammatory and tumorous states. See Lavau, C, et al. (1995) Oncogene 11:871–876; Gambacorta, M, et al. (1996) Am. J. Pathology 149:2023–2035; and Maul, G G, et al. (1995) J. Cellular Biochem. 59:498–513. While the amount of PML is low in normal tissues, an increase in PML expression is observed immumohistochemically in tumors of various origins. See Koken, M H, et al. (1995) Oncogene 10:1315–1324.

Further, it was found that PML is covalently modified by a small polypeptide called SUMO-1, which triggers targeting of PML to its corresponding NBs. See Sternsdorf, T, et al. (1997) J. Cell Bio. 139:1621–1634; Duprez, E, et al. (1999) J. Cell Science 112:381–393; Kretz-Remy, C and Tanguay R M (1999) Biochem. Cell Bio. 77:299–309; and Zhong, S, et al. (2000) Blood 95:2748–2752. SUMO-1 is an ubiquitin-like protein with significant sequence homology to ubiquitin. See Hodges, M, et al. (1998) Current Bio. 8:749–752. Several substrates for SUMO-1 have been reported. See Zhong, S, et al. (2000) blood 95:2748–2752; Desterro, J M, et al. (1998) Mol. Cell Bio. 2:233–239; Saitoh, H, et al. (1998) Current Bio. 8:121–124; Gostissa, M, et al. (1999) EMBO J. 18:6462–6471; and Rodriguez, M S, et al. (1999) EMBO J. 18:6455–6461.

SUMOylation plays a role in multiple vital cellular processes such as oncogenesis, cell cycle control, apoptosis and response to viral infection. Conjugation to SUMO-1 is thought to be a prerequisite for PML to maintain the nuclear body and for subsequent localization of other protein components of the body. In contrast, it has been shown that SUMO-1 modification of PML is not necessary for PML to target the NB. See Ishov A M, et al. (1999) J. Cell Bio. 147:221–233. PML is degraded in cells infected by several viruses. See Everett, R D, et al. (1994) EMBO J. 13:5062–5069; Anh, J H, et al. (1998) Mol. Cell Bio. 18:4899–4913; and Ahn, J H, et al. (1999) J. Virology 73:10458–10471. Infection by a number of DNA viruses triggers the reorganization of the NBs, suggesting an important role for the NBs in the viral infection process. The ability of viral proteins to specifically abrogate the covalent SUMO-1 modification of PML and SP100 is directly linked to their capacity to disassemble NBs. The biological significance of the destruction of the body in viral infection is still unclear.

Immunocytochemical studies to assist in the diagnosis of the progression or extent of the disease are prevalent in the clinical setting, as is the case of breast cancer. To date, while some markers for cervical neoplasia have been reported, their expression is not a footprint for a particular stage of the disease. See Litvinov, S V, et al. (1996) American Journal of Pathology 148:865–875; Skyldberg, B, et al. (1999) J. Nat'l Cancer Inst. 91:1882–1887; Vassallo, J, et al. (2000) International Journal of Gynaecology and Obstetrics 71:45–48; and Klaes, R, et al. (2001) Internat'l J. of Cancer 92:276–284. Immunohistochemical detection of PML expression as a marker for disease progression has focused mainly on hematopoietic malignancies, particularly APL. Although reports on PML in other solid tumor cancers have been documented, neither systematic mapping of the changes in PML throughout the progression of the cancer from CIN to SCC has been performed; nor, has a correlation to its colocalization with SUMO-1. See Saitoh, H, et al. (1998) Current Biol. 8:121–124; and Terris, B, et al. (1995) Cancer Res. 55:1590–1597. These studies also relied on immunohistochemical findings that are graded on the presence or absence of a colorimetric substrate in the nucleus. No spatial or quantitative information at the molecular level of the PML-containing NBs can be acquired from these data.

Thus, a need still exists for methods of detecting PML-containing NBs and methods of diagnosing the different stages of cervical neoplasia and squamous cell carcinoma.

SUMMARY OF THE INVENTION

The present invention provides a method for diagnosing whether an epithelial tissue is an abnormal tissue comprising determining an expression pattern for PML in the epithelial tissue; determining an expression pattern for nuclear bodies in the epithelial tissue; determining SUMO-1 colocalization and comparing the expression pattern for PML and the expression pattern for nuclear bodies with a control. In some preferred embodiments, the control is a normal tissue sample.

In the methods of the present invention, SUMO-1 colocalization of: about 95% indicates that the abnormal tissue is mild dysplasia, moderate dysplasia, or a combination thereof; about 93% indicates that the abnormal tissue is Type A severe dysplasia; about 49% indicates that the abnormal tissue is Type B severe dysplasia; about 18% indicates that the abnormal tissue is cervical squamous cell carcinoma; and about 10% indicates that the abnormal tissue is poorly-differentiated cervical squamous cell carcinoma.

In some preferred embodiments, normal epithelial tissue exhibits a strong expression pattern for PML in the basal layer of the epithelial tissue; basal cells having a consistent PML pattern with an average of about 5 round nuclear bodies per nucleus and an area of about 0.25 $\mu m^2$; a weak expression pattern for PML in the suprabasal and intermediate layers of the epithelial tissue as compared to the expression pattern for PML in the basal layer; no expression of PML in the superficial layer of the epithelial tissue; PML expression in the stroma of the epithelial tissue; a PML expression pattern in the vascular cells of the epithelial tissue similar to the PML pattern in the basal layer; about all of the nuclear bodies comprising PML colocalize with SUMO-1; or a combination thereof.

In some preferred embodiments, the abnormal tissue exhibits PML expression restricted to the lower half of the epithelium of the epithelial tissue; nuclear bodies which have inconsistent shapes; about 9 to about 10 nuclear bodies in the basal layer and upper layer of the epithelial tissue; nuclear bodies having an area of about 0.52 $\mu m^2$ to about 0.54 $\mu m^2$; about 95% or less of the nuclear bodies comprising PML colocalize with SUMO-1; or a combination thereof.

In some embodiments, the abnormal tissue is cervical intraepithelial neoplasia. In other embodiments, the abnormal tissue is mild dysplasia, moderate dysplasia, or a combination thereof.

In some embodiments, the abnormal tissue is Type A severe dysplasia which exhibits PML expression throughout the epithelial tissue; nuclear bodies which have inconsistent shapes and track like structures; about 9 to about 10 nuclear bodies in the basal layer and upper layer of the epithelial tissue; nuclear bodies having an area of about 0.55 $\mu m^2$; about 93% of the nuclear bodies comprising PML colocalize with SUMO-1; or a combination thereof.

In some embodiments, the abnormal tissue is Type B severe dysplasia which exhibits downregulated PML expression; about 5 nuclear bodies in the basal layer and upper layer of the epithelial tissue; nuclear bodies having an area of about 0.33 $\mu m^2$; about 49% of the nuclear bodies comprising PML colocalize with SUMO-1; or a combination thereof.

In some embodiments, the abnormal tissue is well-differentiated cervical squamous cell carcinoma which exhibits upregulated PML expression; variation in the number and size of nuclear bodies; about 9 nuclear bodies in the epithelial tissue; nuclear bodies having an area of about 0.73 $\mu m^2$; about 18% of the nuclear bodies comprising PML colocalize with SUMO-1; or a combination thereof.

In some embodiments, the abnormal tissue is poorly-differentiated cervical squamous cell carcinoma which exhibits downregulated PML expression; about 5 nuclear bodies in the epithelial tissue; nuclear bodies having an area of about 0.37 $\mu m^2$; about 10% of the nuclear bodies comprising PML colocalize with SUMO-1; or a combination thereof.

In some preferred embodiments, the PML expression pattern and SUMO-1 colocalization are fluorescently detected in a paraffin embedded tissue biopsy of the epithelial tissue.

In some embodiments, the present invention provides a method for diagnosing whether a subject has mild dysplasia, moderate dysplasia, Type A severe dysplasia, Type B severe dysplasia, cervical squamous cell carcinoma, or poorly-differentiated cervical squamous cell carcinoma comprising determining an expression pattern for PML in an epithelial tissue sample from the subject; determining an expression pattern for nuclear bodies in the epithelial tissue; determining SUMO-1 colocalization; and determining whether the expression pattern for PML, the expression pattern for nuclear bodies, and the SUMO-1 colocalization of the epithelial tissue sample is consistent with expression patterns expected for mild dysplasia, moderate dysplasia, Type A severe dysplasia, Type B severe dysplasia, cervical squamous cell carcinoma, or poorly-differentiated cervical squamous cell carcinoma.

In some embodiments, SUMO-1 colocalization of about 95% indicates that the subject has mild dysplasia, moderate dysplasia, or a combination thereof, SUMO-1 colocalization of about 93% indicates that the subject has Type A severe dysplasia; SUMO-1 colocalization of about 49% indicates that the subject has Type B severe dysplasia; SUMO-1 colocalization of about 18% indicates that the subject has cervical squamous cell carcinoma; and SUMO-1 colocalization of about 10% indicates that the subject has poorly-differentiated cervical squamous cell carcinoma.

In some embodiments of the present invention, PML expression restricted to the lower half of the epithelium of the epithelial tissue; nuclear bodies which have inconsistent shapes; about 9 to about 10 nuclear bodies in the basal layer and upper layer of the epithelial tissue; nuclear bodies having an area of about 0.52 $\mu m^2$ to about 0.54 $\mu m^2$; about 95% of the nuclear bodies comprising PML colocalize with SUMO-1; or a combination thereof indicates that the subject has mild dysplasia, moderate dysplasia, or a combination thereof.

In some embodiments of the present invention, PML expression throughout the epithelial tissue; nuclear bodies which have inconsistent shapes and track like structures; about 9 to about 10 nuclear bodies in the basal layer and upper layer of the epithelial tissue; nuclear bodies having an area of about 0.55 $\mu m^2$; about 93% of the nuclear bodies comprising PML colocalize with SUMO-1; or a combination thereof indicates that the subject has Type A severe dysplasia.

In some embodiments of the present invention, downregulated PML expression; about 5 nuclear bodies in the basal layer and upper layer of the epithelial tissue; nuclear bodies having an area of about 0.33 $\mu m^2$; about 49% of the nuclear bodies comprising PML colocalize with SUMO-1; or a combination thereof indicates that the subject has Type B severe dysplasia.

In some embodiments of the present invention, upregulated PML expression; variation in the number and size of nuclear bodies; about 9 nuclear bodies in the epithelial tissue; nuclear bodies having an area of about 0.73 $\mu m^2$; about 18% of the nuclear bodies comprising PML colocalize with SUMO-1; or a combination thereof indicates that the subject has well-differentiated cervical squamous cell carcinoma.

In some embodiments of the present invention, downregulated PML expression; about 5 nuclear bodies in the epithelial tissue; nuclear bodies having an area of about 0.37 $\mu m^2$; about 10% of the nuclear bodies comprising PML colocalize with SUMO-1; or a combination thereof indicates that the subject has poorly-differentiated cervical squamous cell carcinoma.

In preferred embodiments of the present invention, the subject is mammalian, more preferably human.

In some embodiments, the present invention relates to methods of treating a subject suffering from or being diagnosed with abnormal epithelial tissue comprising determining whether the abnormal epithelial tissue is mild dysplasia, moderate dysplasia, Type A severe dysplasia, Type B severe dysplasia, well-differentiated cervical squamous cell carcinoma, or poorly-differentiated cervical squamous cell carcinoma and then treating the subject accordingly. In some embodiments, the subject is treated with chemotherapy. In some embodiments, the abnormal epithelial tissue is destroyed or removed. In some embodiments, a hysterectomy is conducted on the subject.

It is to be understood that both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention and together with the description serve to explain the principles of the invention.

DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
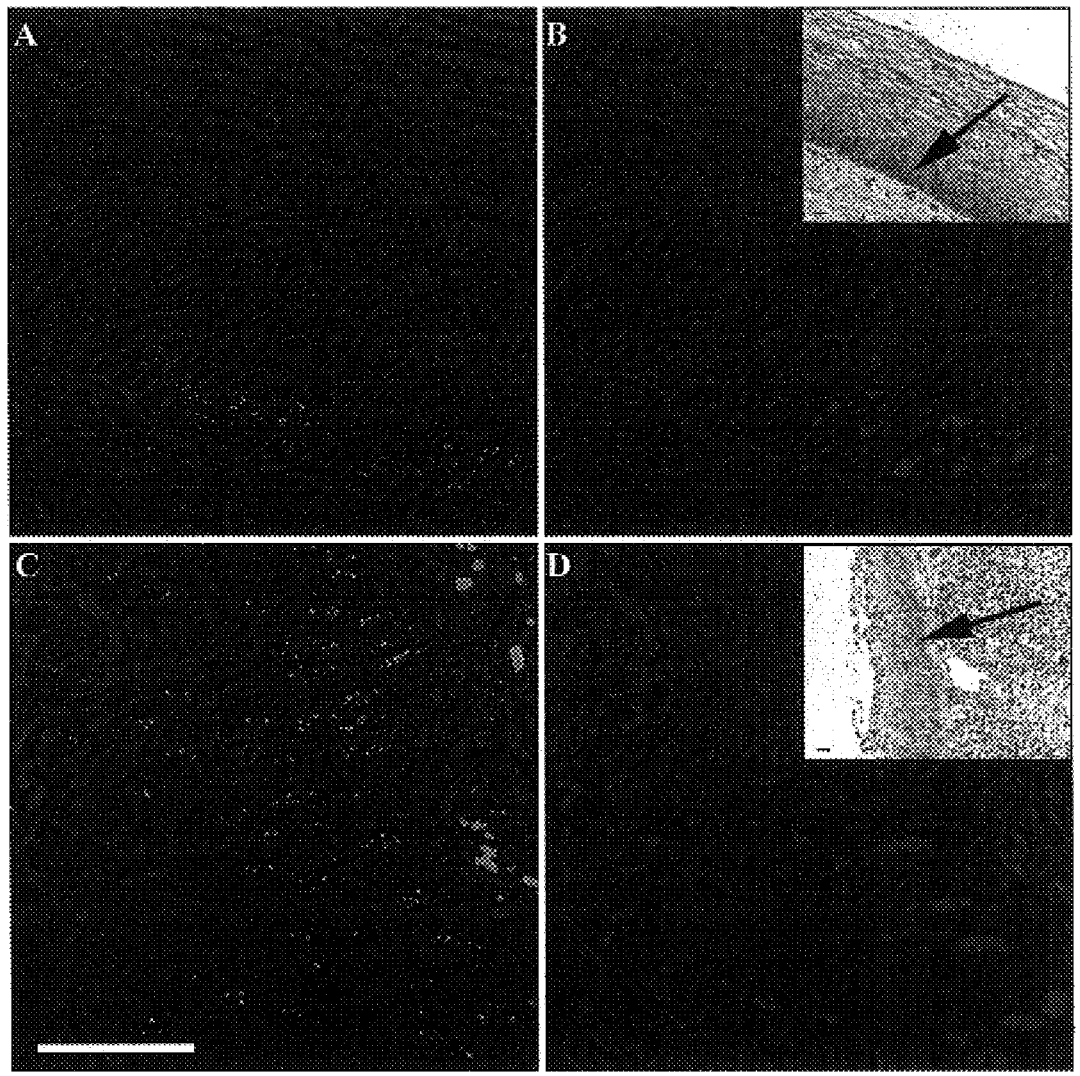
FIG. 1 is a micrograph showing PML and SUMO-1 expression in normal and CIN I/CIN II cervical epithelium. True focus fluorescent micrographs of PML (green) overlayed on phase contrast image (blue) (A) and SUMO-1 (red) (B) in normal epithelium. True focus fluorescent micrographs of PML (green) overlayed on phase contrast image (blue) (C) and SUMO-1 (red) (D) in CIN I/CINII cervical epithelium. Corresponding H&E's with arrow indicating the region where fluorescent image was taken. White and black size bars are 20 μm.

The present invention relates to a fluorescence-based method for the detection of the nuclear bodies (NBs) containing promyelocyte (PML) protein. In particular, the present invention provides methods diagnosing the different stages of cervical neoplasia and squamous cell carcinoma which comprises detecting and analyzing the number and size of PML containing NBs, and the change in PML partnership with SUMO-1.

As provided herein, PML and SUMO-1 distribution exhibit significant changes that parallel the stepwise progression of cervical neoplasia towards malignant transformation. In cervical squamous cell carcinoma, PML and SUMO-1 reflect the differential phenotype of malignant cells and specifically the aggressiveness of the tumor, i.e. well- versus poorly-differentiated tumors. While the function of PML and its nuclear body remains to be defined, as provided herein, the distribution of PML is affected in cervical dysplasia and squamous cell carcinoma. In general, there is an increase in number and size of PML bodies as normal cervical tissue progresses to CIN I/CIN II. In CIN III, two subcategories emerge with distinctly different PML patterns with the Type B CIN III losing SUMO-1 partnership with PML as compared to Type A. In SCC, there is a loss of PML/SUMO-1 partnership in both well- and poorly-differentiated tumors with a distinctly different PML pattern. Well-differentiated tumors have bigger bodies which are more in number than that of the poorly-differentiated tumors.

As provided below, PML distribution reflects a differential phenotype in cervical tumors, which is dependent on the tumor grading. The weaker immunoreactivity in tumor cells of poorer differentiation is consistent with the notion that PML, being a regulatory protein, might be turned off in tumorous states that go in parallel with unregulated proliferation, increased mitotic rates, and loss of differentiation. One even more striking observation is the irregularity of the shapes of NBs, which varies from cell to cell in poorly-differentiated tumors. Abnormal track-like structures containing PML are observed, which is consistent with those seen in viral infection. Thus, the decreased size of the NBs and this track-like distribution may reflect an aggressive type of tumor that is distinctively different from the well-differentiated SCC.

Also, as provided below, distant metastatic sites (secondary tumors) display different PML expression compared to their primary tumors. This implicates that one tumor does not have a characteristic PML pattern, which is in accordance with the notion that a tumor has different phenotypes and that metastatic cells have other abilities than primary tumors, supporting the ability to metastasize requires additional mutations or epigenetic changes.

As provided below, well-differentiated tumors may follow a different disease progression than poorly-differentiated tumors which may be the reason for the two distinct staining patterns in CIN III. Thus, well-differentiated tumors may progress from Type A CIN III, which is characterized by a sustained increase in PML body number and size. In contrast, Type B CIN III may progress to a more aggressive, poorly-differentiated tumor.

As provided herein, PML is closely involved in the tumorigenesis of cervical carcinoma. Changes in PML are not restricted to up and down regulation of the nuclear protein, but rather to its distribution, i.e., size, shape, number and its ability to associate with SUMO-1.

Therefore, the present invention provides a method of detecting or diagnosing normal squamous epithelium in a subject comprising analyzing the PML pattern and NB size and shape in the epithelium of the subject and SUMO-1 colocalization. In some preferred embodiments, the basal cells of normal squamous epithelium exhibit a consistent PML pattern with about 5 round NBs each having an area of about 0.25 $\mu m^2$. In some preferred embodiments, the suprabasal and intermediate layers of normal squamous epithelium comprise fewer cells that are positive for PML, and, those cells that are positive have statistically fewer NBs, about 3 NBs/nuclei ($p<0.001$) each having an area of about 0.22 $\mu m^2$. In some embodiments, the method further comprises determining whether the NB's comprising PML colocalize with SUMO-1. In some preferred embodiments, all of the PML-containing NBs colocalize with SUMO-1 in normal squamous epithelium.

In some embodiments, the present invention provides a method of detecting or diagnosing CIN I/CIN II in a subject comprising analyzing the PML pattern and NB size and shape in the epithelium of the subject. In some preferred embodiments, PML is restricted to the lower half of the epithelium and the NBs are not consistently round in CIN I/CIN II. In some preferred embodiments, the NBs are dramatically increased (about double) in number and size in CIN I/CIN II as compared to normal basal and upper layers. In some preferred embodiments, there are about 9 NBs per nucleus having an area of about 0.52 $\mu m^2$ in the nuclei of the basal layer and about 10 NBs having an area of about 0.54 $\mu m^2$ in the nuclei in upper layers. In CIN I/CIN II, SUMO-1 is further recruited to the NBs with 95% colocalization.

In some embodiments, the present invention provides a method of detecting or diagnosing CIN III in a subject comprising analyzing the PML pattern and NB size and shape in the epithelium of the subject. In some preferred embodiments, PML positively extends the full thickness of CIN III epithelium. In some embodiments, the method further comprises analyzing whether the CIN III epithelium is Type A CIN III or Type B CIN III. In Type A, the cells comprise about 9 NBs containing PML that have an area of about 0.55 $\mu m^2$, wherein the NBs are significantly larger and more in number than those of normal epithelium. In some preferred embodiments, the size and shape of the NBs in Type A CIN III are highly irregular and there is an increase in the appearance of track-like structures. Additionally, in Type A CIN III, SUMO-1 colocalizes with the NBs containing PML in about 93% of the cells. In Type B CIN III, the number of NBs is about 5 per nucleus with an area of about 0.33 $\mu m^2$ (similar to normal epithelium). In Type B CIN III, SUMO-1 colocalization dropped to 49% of the cells.

In some embodiments, the present invention provides a method of detecting or diagnosing well-differentiated cervical squamous cell carcinoma (CA+) in a subject comprising analyzing the PML pattern and NB size and shape in the epithelium of the subject. In some preferred embodiments, there are about 9 NBs with an area of about 0.73 $\mu m^2$ per nucleus in CA+. In some preferred embodiments, there is a greater variation in the number of bodies and size in CA+ as compared to normal epithelium. In some preferred embodiments, the average size of the NB is significantly larger than normal. In some preferred embodiments, SUMO-1 colocalization is about 18% in CA+.

In some embodiments, the present invention provides a method of detecting or diagnosing poorly-differentiated cervical squamous cell carcinoma (CA−) in a subject comprising analyzing the PML pattern and NB size and shape in the epithelium of the subject. In some preferred embodiments, there are about 5 NBs per nucleus with an area of about 0.37 $\mu m^2$. In some preferred embodiments, only about 10% of cells exhibited colocalization with SUMO-1.

The following examples are intended to illustrate but not to limit the invention.

EXAMPLE 1

Immunodetection Assays

Immunodetection studies were performed on paraffin-embedded pathological human uterine cervix tissues. All samples were obtained from the archival files of the Department of Pathology, University Hospital Zurich, Switzerland. Specimens were graded on the Bethesda scale from a hematoxylin and eosin (H&E) stained slide by a certified pathologist. Institutional approval was granted by UC Irvine Institutional Review Board Administration for these studies.

Resection specimens of 12 subjects with normal tissue, 33 subjects with cervical intraepithelial neoplasia (CIN I–III), 20 subjects with cervical squamous cell carcinoma spanning from early invasive carcinoma to metastasizing cervical tumors, and 10 pairs of primary tumors with corresponding metastasis were analyzed. All specimens were fixed in phosphate buffered 4% formaldehyde solution and paraffin-embedded for histological and immunofluorescence detection by methods standard in the art.

A. Histology and Immunofluorescence

Sections were cut (5 μm thick), floated on poly-L-lysine-coated glass microscope slides, and air dried overnight at room temperature. Sections from paraffin blocks were dewaxed in Histo-Clear (National Diagnostics, Atlanta, Ga.) and rehydrated through grades of alcohols to deionized water. Hematoxylin and eosin staining was performed by methods standard in the art. For immunodetection, slides were rinsed in PBS, and antigen retrieval (BioGenex, San Ramon, Calif.) was performed by microwave pressure cooking for about 30 minutes. Nonspecific binding was blocked by 20% normal swine serum/PBS. Sections were incubated with an affinity-purified rabbit polyclonal IgG (a kind gift of Dr. J. Dyck) raised against amino acid residues 1–14 of the PML protein for 2 hours at 37° C. See Dyck J A, et al. (1994) Cell 76:333–343, which is herein incorporated by reference. Rabbit IgG was detected with a fluorescent secondary Cy3-conjugated anti-rabbit IgG (Molecular Probes, Eugene, Oreg.). Coverslips were mounted with vectashield mounting medium (Vector Laboratories, Burlingame, Calif.). Negative controls consisted of replacement of primary antibody with normal rabbit serum. SUMO-1 was detected with a mouse monoclonal antibody (Zymed Laboratories, San Francisco, Calif.) and a secondary antibody conjugated to Alexa 488 fluorophore (Molecular Probes, Eugene, Oreg.).

B. Immunofluorescence Detection

Fluorescently labeled samples were examined by an inverted Zeiss laser scanning microscope LSM 410 (Carl Zeiss, Oberkochen, Germany). The objective used was an oil immersion 100× magnification Plan-Neofluar Phase 3, n. a. 1.3 (Carl Zeiss, Oberkochen, Germany). Stacks of thin optical sections were obtained for each sample. The 488 nm line of an Argon laser was used for simultaneous excitation of both fluorophores (Cy-3 and Alexa 488). Simultaneously detected red and green emissions were isolated by a long-pass 610 nm filter and by a narrow band-pass (530 nm band center) filter, respectively; blue channel was used for a non-confocal phase-contrast image acquisition. Fluorescent images were pseudocolored green and red and overlayed with the phase contrast image. The distance between two consecutive optical sections was 0.5 μm on the Z axis. Overall depth of acquisition ranged from about 0 to about 5 μm, covering the whole thickness of a sample. The "true-focus" images were generated from stacks of stored images using the original LSM 410 software. H&E images were obtained with an Olympus DP10 microscope digital camera system (Olympus, Melville, N.Y.) and a S Plan40xPL/0.70 objective. Scale bars (20 μm) were added to both the phase contrast and fluorescence image for comparison.

C. Image Analysis

True-focus images of NB-associated fluorescence, obtained from a confocal scanning microscope were post-processed using scientific imaging software, IPLabs (version 3.5.5, Scanalytics, Inc, Fairfax, Va.). Due to the nature of sectioning of the tissue blocks, only whole cells were selected for analysis. Images were segmented, i.e. target pixels were separated from background pixels based on their values. Segmentation was based on the intensity of the fluorescence signal. Segments were quantified by an area (in $\mu m^2$) and number per selected whole cell. Single pixels with high numerical values (background noise) were eliminated from counting by introducing a limiting criterion (minimal area). Random cells were selected from the appropriate H&E area and quantitatively analyzed for the average number of bodies and the average area of the bodies. In all categories an average of 54 cells/subject was analyzed with a total of 25,648 bodies measured.

D. Results

Figure 2:
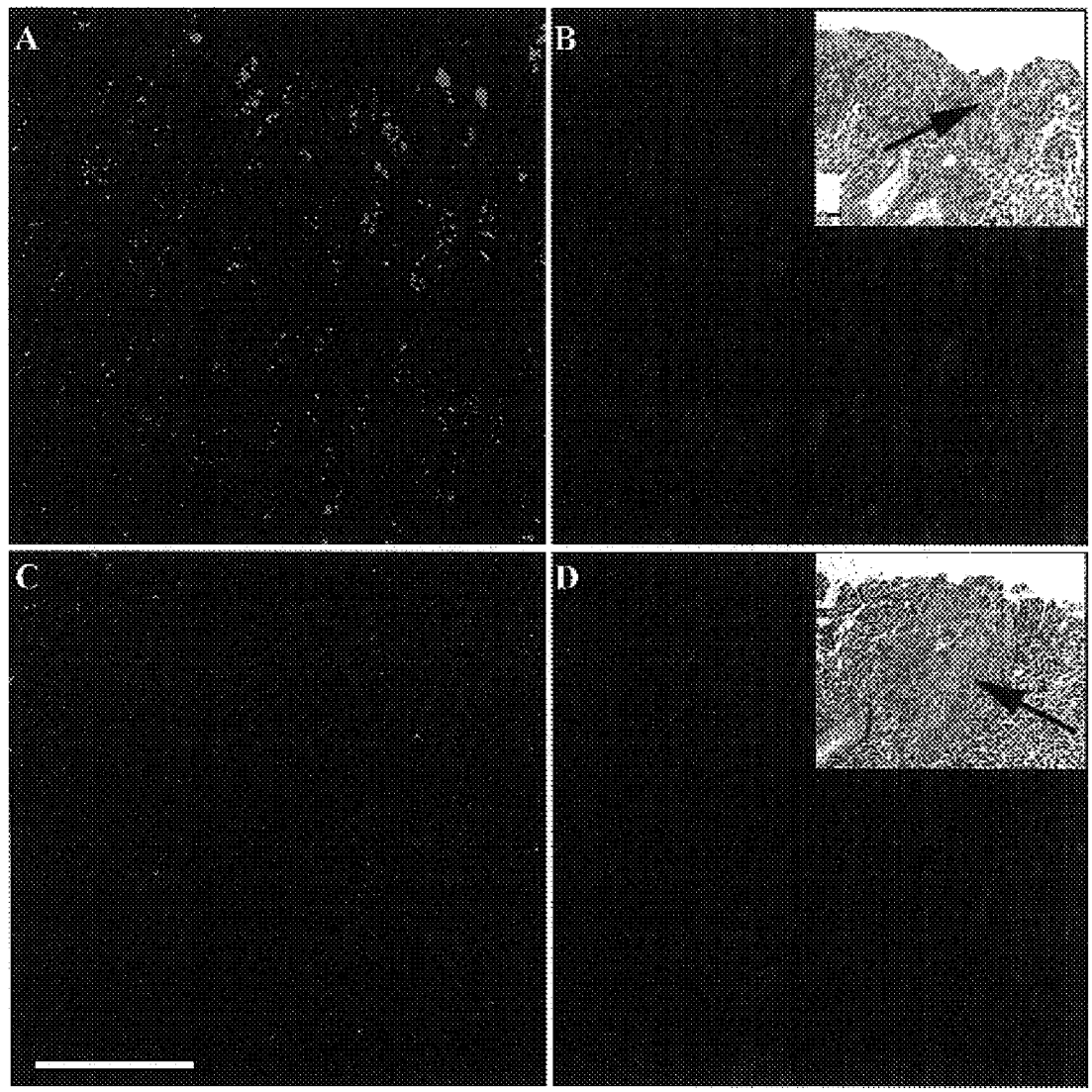
FIG. 2 is a micrograph showing PML and SUMO-1 expression in Type A and Type B CIN III cervical epithelium. True focus fluorescent micrographs of PML (green) overlayed on phase contrast image (blue) (A) and SUMO-1 (red) (B) in Type A CIN III epithelium. True focus fluorescent micrographs of PML (green) overlayed on phase contrast image (blue) (C) and SUMO-1 (red) (D) in Type B CIN III epithelium. Corresponding H&E's with arrow indicating the region where fluorescent image was taken. White and black size bars are 20 μm.
Figure 3:
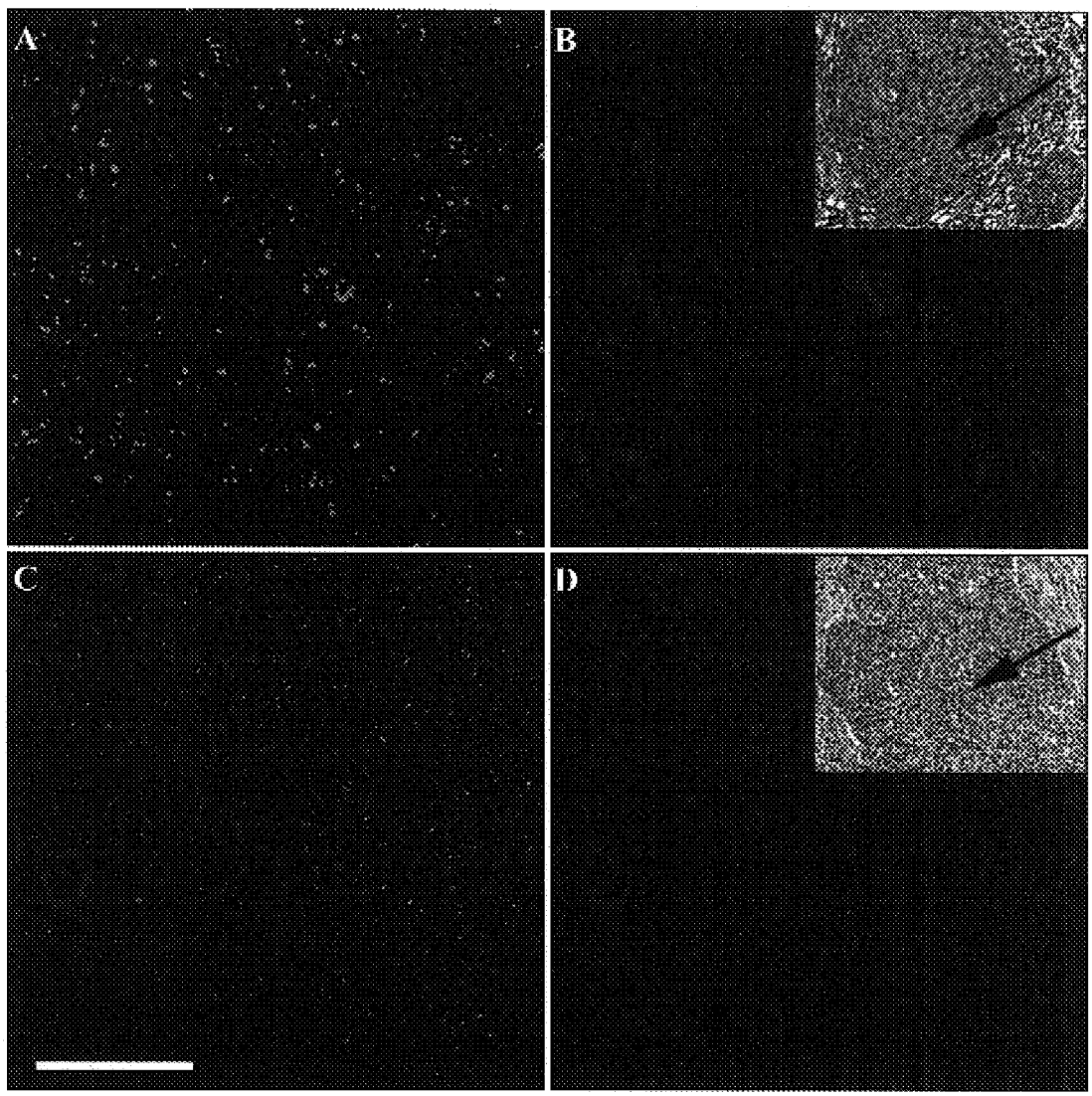
FIG. 3 is a micrograph showing PML and SUMO-1 expression in well-differentiated and poorly-differentiated squamous cell cervical carcinoma. True focus fluorescent micrographs of PML (green) overlayed on phase contrast image (blue) (A) and SUMO-1 (red) (B) in well-differentiated carcinoma (CA+). True focus fluorescent micrographs of PML (green) overlayed on phase contrast image (blue) (C) and SUMO-1 (red) (D) in poorly-differentiated carcinoma (CA−). Corresponding H&E's with arrow indicating the region where fluorescent image was taken. White and black size bars are 20 μm.

FIGS. 1–3 are representative true-focus fluorescent micrographs of PML (green) and SUMO-1 (red) with the corresponding H& E image (insets). In particular, FIG. 1 shows PML and SUMO-1 expression in normal epithelium and CIN I/CINII cervical epithelium. FIG. 1A shows a true focus fluorescent micrograph of PML (green) overlayed on phase contrast image (blue) and FIG. 1B shows SUMO-1 (red) in normal epithelium. FIG. 1C shows a true focus fluorescent micrographs of PML (green) overlayed on phase contrast image (blue) and FIG. 1D shows SUMO-1 (red) in CIN I/CIN II cervical epithelium. Corresponding H&E's with arrow indicating the region where fluorescent image was taken. White and black size bars are 20 μm.

FIG. 2 shows PML and SUMO-1 expression in Type A and Type B CIN III cervical epithelium. In particular, FIG. 2A shows a true focus fluorescent micrograph of PML (green) overlayed on phase contrast image (blue) and FIG. 2B shows SUMO-1 (red) in Type A CIN III epithelium. FIG. 2C shows a true focus fluorescent micrograph of PML (green) overlayed on phase contrast image (blue) and FIG. 2D shows SUMO-1 (red) in Type B CIN III epithelium. Corresponding H&E's with arrow indicating the region where fluorescent image was taken. White and black size bars are 20 μm.

FIG. 3 shows PML and SUMO-1 expression in well-differentiated and poorly-differentiated squamous cell cervical carcinoma. FIG. 3A is a true focus fluorescent micrographs of PML (green) overlayed on phase contrast image (blue) and FIG. 2B is SUMO-1 (red) in well-differentiated carcinoma (CA+). FIG. 3C is a true focus fluorescent micrograph of PML (green) overlayed on phase contrast image (blue) and FIG. 3D is SUMO-1 (red) in poorly-differentiated carcinoma (CA−). Corresponding H&E's with arrow indicating the region where fluorescent image was taken. White and black size bars are 20 μm.

Figure 4:
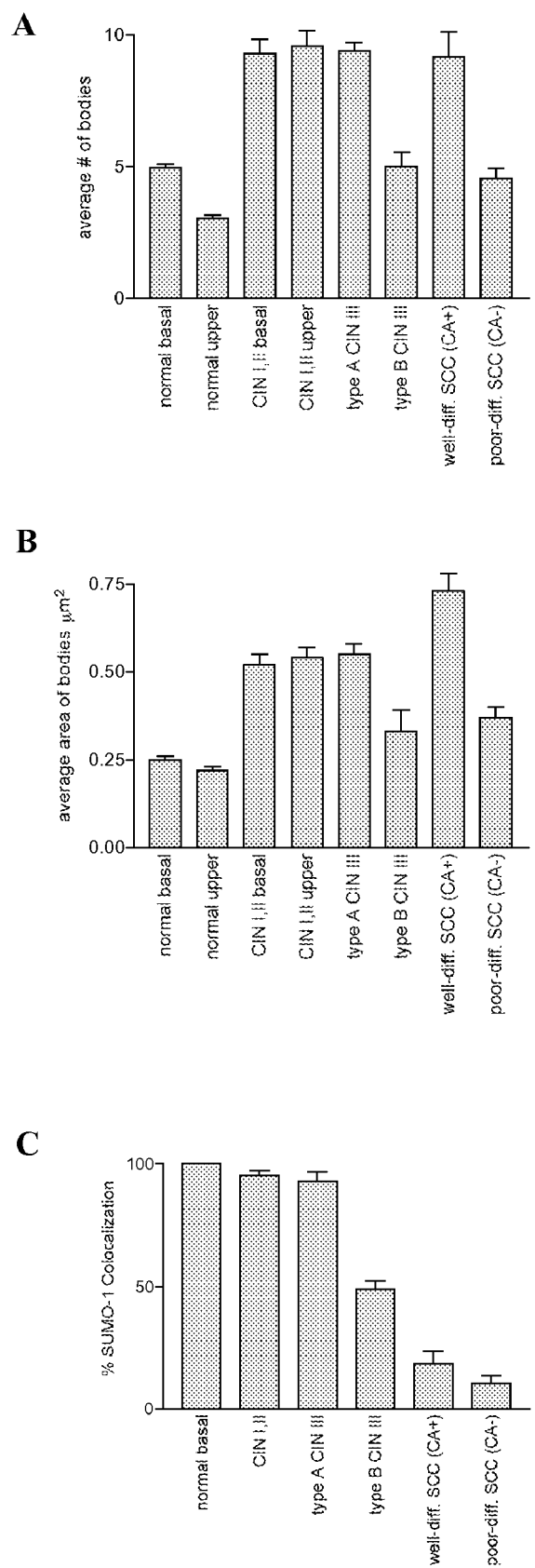
FIG. 4 provides bar graphs of the analysis of PML and SUMO-1 expression. The average number of PML bodies±the standard error (SE) (A), the average area ($\mu m^2$) of a body±the SE (B) and the average percentage of cells that have PML colocalizing with SUMO-1±the SE (C).

FIG. 4 provides the analysis of PML and SUMO-1 expression. In particular, FIG. 4A shows the average number of PML bodies±the standard error (SE). FIG. 4B shows the average area ($\mu m^2$) of a body±the SE. FIG. 4C shows the average percentage of cells that have PML colocalizing with SUMO-1±the SE.

1. Normal Squamous Tissue (12 Cases)

As shown in FIG. 1A, PML displays the strongest immunoreactivity in the basal layer of the squamous epithelium. Here, basal cells show a consistent PML pattern with an average of about 5 round NBs per nucleus and an area of 0.25 $\mu m^2$ (FIG. 4A, FIG. 4B). This is consistent with the average reported size of a PML body of 0.5 to 1 micron in diameter. The suprabasal and intermediate layers display less staining for PML in that there are fewer cells that are positive for PML, and, those that are positive have statistically fewer bodies (3 NBs /nuclei) ($p<0.001$). These bodies are, however, comparable in size (0.22 $\mu m^2$) to those in the basal layer. The superficial layer is PML negative. PML is also positive throughout the stroma. Vascular cells display the same intensity of staining as the basal cells of the normal epithelium (not shown), which also serves as a positive control. Cells of the connective tissue exhibit less intense fluorescence. About all of the PML-containing NBs colocalize with SUMO-1 (FIG. 1B; FIG. 4C). Since SUMO-1 modifies other proteins, it is present in other regions of the nucleus in addition to the PML-containing NBs.

2. CIN I/CIN II (15 Cases)

Morphologically a CIN I/CIN II lesion is close to normal epithelium, in that histologically the basal layer can be distinguished from the upper layers. Consequently, the PML and SUMO-1 staining for the basal and the upper layers was analyzed separately for comparison to normal. In CIN I/CIN II, PML is restricted to the lower half of the epithelium and no longer are the NBs always perfectly round (FIG. 1C). The NBs are dramatically increased (doubled) in number and size as compared to normal basal and upper layers respectively ($p<0.001$). An average of about 9 bodies per nucleus (0.52 $\mu m^2$) are in the nuclei of the basal layer and about 10 bodies (0.54 $\mu m^2$) in the nuclei in upper layers (FIG. 4A). The basal and upper areas of CIN I/CIN II are not statistically different from each other. SUMO-1 appears to be further recruited to the NBs as a result of their increase in size (FIG. 1D) with 95% colocalization (FIG. 4C).

3. CIN III(Severe Dysplasia) (18 Cases)

In grade III lesions, PML positivity extended the full thickness of the epithelium. After analysis of the 18 subject samples, the data fell logically into two subgroups, which are classified as Type A (10 cases) and Type B (8 cases) CIN III. Type A CIN III was statistically similar to CIN I/CIN II with an average of about 9 PML-containing NBs that were 0.55 $\mu m^2$ in area (FIG. 2A; FIG. 4A, FIG. 4B). The NBs remained significantly larger and more in number than those of normal epithelium ($p<0.001$). The size and shape showed high irregularity, with an increase in the appearance of track-like structures. These structures were not resolvable by confocal microscopy because of the limitations of pixel size. SUMO-1 continued to colocalize with the PML-containing NBs in 93% of the cells (FIG. 2B, FIG. 4C).

In Type B CIN III, the PML body size and number are dramatically downregulated (FIG. 2C). The number of NBs falls to an average of about 5 per nucleus with an average size of 0.33 $\mu m^2$ (FIG. 4A, FIG. 4B). Both the area and number are comparable to those for normal epithelium (p value not significant, see Table 1). The number of NBs is significantly different from CIN I, CIN II and Type A CIN III ($p<0.01$ and $p<0.001$, respectively). The decreased area is statistically significant from CIN I/CIN II upper ($p<0.05$) and very close to significance with p values of 0.0049 and 0.0038, respectively, as compared to CIN I/CIN II basal and Type A CIN III. In Type B CIN III, as PML body size and number were downregulated, SUMO-1 colocalization dropped to about 49% of the cells clearly differentiating it from Type A CIN III. This loss of partnership and change in PML pattern suggests new subcategories of neoplasia.

4. Cervical Squamous Carcinoma (20 Cases)

4a. Well-Differentiated Cervical Squamous Cell Carcinoma (CA+)

Eleven cases of well-differentiated tumors were analyzed. Here, PML body size and number are increased (FIG. 3A). There are on average about 9 NBs of 0.73 $\mu m^2$ in area per nucleus (FIG. 4A, FIG. 4B). There is a greater variation in the number of bodies and size. Some cells exhibit few in number and large NBs. The average number of bodies is significantly different from normal epithelium ($p<0.05$) and nearly significant from Type B CIN III ($p=0.0032$). The average size of the NB is significantly larger than normal ($p<0.001$), CIN I/CIN II ($p<0.05$), and Type B CIN III ($p<0.01$). SUMO-1 colocalization with the PML-containing NB is lost with only about 18% of the cells exhibiting SUMO-1 colocalization (FIG. 3B, FIG. 4C).

4b. Poorly-Differentiated Cervical Squamous Cell Carcinoma (CA−)

Nine cases of poorly differentiated carcinomas were analyzed. As in Type B CIN III, and in contrast to a well-differentiated tumor, PML body number and size remain lower with an average of about 5 NBs per nucleus of 0.37 $\mu m^2$ in area (FIG. 3C, FIG. 4A, FIG. 4B). As expected, the size and number of NBs are not statistically different from Type B CIN III if a progression from Type B CIN III to SCC is predicted. In contrast they were statistically different from the well-differentiated tumors in number of NBs and area ($p<0.05$, $p<0.01$) as well as Type A CIN III ($p<0.001$, $p<0.05$). Poorly-differentiated CA− had significantly fewer NBs than CIN I/CIN II ($p<0.001$) while the area was almost significantly less ($p=0.006$). In agreement with progressive neoplasia, SUMO-1 colocalization with the PML-containing NB is lost with only about 10% of the cells exhibiting SUMO-1 colocalization (FIG. 3D, FIG. 4C).

5. Primary and Secondary Tumors

In addition, 10 cases of primary and secondary tumors were examined for differences in PML pattern. In some cases, immunohistochemistry showed differences in PML expression, i.e. size and number of bodies, between primary tumors and their metastases; but, in some cases the pattern was the same. Differences in pattern could not be attributed to location of the metastases. In addition, for all cases, no correlation was found between the stage of tumor (Ib, II, III), age of subject, or presence of HPV infection as previously assessed diagnostically by PCR.

E. Statistical Analysis

Average number and area of the PML-containing NB for each subject was calculated as described above.

The seven subject groups, normal basal (12), normal upper (12), CIN I/CIN II basal (15), CIN I/CIN II upper (15), CIN III (18), well-differentiated squamous cell carcinoma, (CA+) (11), poorly-differentiated squamous cell carcinoma, (CA−) (9) were statistically compared by pairwise t-tests with a Bonferroni correction for multiple comparisons. Out of 28 possible comparisons, 6 comparisons were eliminated since comparison would not be relevant (as indicated with a hatched area in Table 1). Using the Bonferroni method of correction for multiple comparisons, a single comparison must be significant with $p<0.05/22$ or $p<0.0023$ in order to maintain an overall type 1 error rate of 5%. A separate variance estimate is used in the t-test whenever indicated by significance of the Levene test for equality of variances (*); otherwise, a pooled estimate is used for the variance. Table 1 summarizes the results of the ANOVA statistical analysis performed on the data provided in FIG. 4A.

TABLE 1

| # | normal upper 3.05 | CIN I,II basal 9.29 | CIN I,II upper 9.57 | Type A CIN III 9.39 | Type B CIN III 5.01 | CA+ 9.16 | CA- 4.56 |
|---|---|---|---|---|---|---|---|
| normal basal 4.97 | $p < 0.001$ | $p < 0.001$* | | $p < 0.001$ | ns* | $p < 0.05$* | ns* |
| normal upper 3.05 | | $p < 0.001$* | $p < 0.001$* | n* | | | |
| CIN I,II basal 9.29 | | | ns | ns* | $p < 0.01$ | ns | $p < 0.001$ |
| CIN I,II upper 9.57 | | | | ns* | $p < 0.01$ | | |
| Type A CIN III 9.39 | | | | | $p < 0.001$ | ns | $p < 0.001$ |
| Type B CIN III 5.01 | | | | | | ns | ns |
| CA+ 9.16 | | | | | | | $p < 0.05$* |

Table 2 summarizes the results of the ANOVA statistical analysis performed on the data provided in FIG. 4B.

TABLE 2

| area μm² | normal upper 0.22 | CIN I,II basal 0.52 | CIN I,II upper 0.54 | Type A CIN III 0.55 | Type B CIN III 0.33 | CA+ 0.73 | CA- 0.37 |
|---|---|---|---|---|---|---|---|
| normal basal 0.25 | ns | $p < 0.001$* | | $p < 0.001$* | ns* | $p < 0.001$* | ns* |
| normal upper 0.22 | | $p < 0.001$* | $p < 0.001$* | ns* | | | |
| CIN I,II basal 0.52 | | | ns | ns | ns | $p < 0.05$ | ns |
| CIN I,II upper 0.54 | | | | ns | $p < 0.05$ | | |
| Type A CIN III 0.55 | | | | | ns | ns | $p < 0.05$ |
| Type B CIN III 0.33 | | | | | | $p < 0.01$ | ns |
| CA+ 0.73 | | | | | | | $p < 0.01$ |

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for diagnosing whether an epithelial tissue is an abnormal tissue comprising determining an expression pattern for PML in the epithelial tissue;

determining an expression pattern for nuclear bodies in the epithelial tissue;

determining a loss of SUMO-1 colocalization with nuclear bodies comprising PML in the epithelial tissue; and comparing the expression pattern for PML, the expression pattern for nuclear bodies, and the loss of SUMO-1 colocalization with nuclear bodies comprising PML with that of a normal tissue, where loss of SUMO-1 colocalization with nuclear bodies comprising PML indicates abnormal tissue.

2. The method of claim 1, wherein the expression patterns of the normal tissue is determined from a normal tissue sample.

3. The method of claim 1, wherein the normal tissue exhibits (a) a strong expression pattern for PML in the basal layer of the epithelial tissue;
(b) basal cells having a consistent PML pattern with an average of about 5 round nuclear bodies per nucleus and an area of about 0.25 µm$^2$;
(c) a weak expression pattern for PML in the suprabasal and intermediate layers of the epithelial tissue as compared to (a);
(d) no expression of PML in the superficial layer of the epithelial tissue;
(e) PML expression in the stroma of the epithelial tissue;
(f) a PML expression pattern in the vascular cells of the epithelial tissue similar to (a);
(g) about all of the nuclear bodies comprising PML colocalize with SUMO-1; or
(h) a combination thereof.

4. The method of claim 1, wherein the abnormal tissue exhibits
(a) PML expression restricted to the lower half of the epithelium of the epithelial tissue;
(b) nuclear bodies having irregular shapes;
(c) about 9 to about 10 nuclear bodies in the basal layer and upper layer of the epithelial tissue;
(d) nuclear bodies having an area of about 0.52 µm$^2$ to about 0.54 µm$^2$;
(e) about 95% of the nuclear bodies comprising PML colocalize with SUMO-1; or
(f) a combination thereof.

5. The method of claim 1, wherein the abnormal tissue is cervical intraepithelial neoplasia.

6. The method of claim 4, wherein the abnormal tissue is mild dysplasia, moderate dysplasia, or a combination thereof.

7. The method of claim 1, wherein the epithelial tissue exhibits
(a) PML expression throughout the epithelial tissue;
(b) nuclear bodies having irregular shapes and nuclear bodies having track-like structures;
(c) about 9 to about 10 nuclear bodies in the basal layer and upper layer of the epithelial tissue;
(d) nuclear bodies having an area of about 0.55 µm$^2$;
(e) about 93% of the nuclear bodies comprising PML colocalize with SUMO-1; or
(f) a combination thereof which is abnormal tissue.

8. The method of claim 7, wherein the abnormal tissue is Type A severe dysplasia.

9. The method of claim 1, wherein the epithelial tissue exhibits
(a) downregulated PML expression;
(b) about 5 nuclear bodies in the basal layer and upper layer of the epithelial tissue;
(c) nuclear bodies having an area of about 0.33 µm$^2$;
(d) about 49% of the nuclear bodies comprising PML colocalize with SUMO-1; or
(e) a combination thereof, which is abnormal tissue.

10. The method of claim 9, wherein the abnormal tissue is Type B severe dysplasia.

11. The method of claim 1, wherein the epithelial tissue exhibits
(a) upregulated PML expression;
(b) variation in the number and size of nuclear bodies;
(c) about 9 nuclear bodies in the epithelial tissue;
(d) nuclear bodies having an area of about 0.73 µm$^2$;
(e) about 18% of the nuclear bodies comprising PML colocalize with SUMO-1; or
(f) a combination thereof which is abnormal tissue.

12. The method of claim 11, wherein the abnormal tissue is well-differentiated cervical squamous cell carcinoma.

13. The method of claim 1, wherein the abnormal tissue exhibits
(a) downregulated PML expression;
(b) about 5 nuclear bodies in the epithelial tissue;
(c) nuclear bodies having an area of about 0.37 µm$^2$;
(d) about 10% of the nuclear bodies comprising PML colocalize with SUMO-1; or
(e) a combination thereof.

14. The method of claim 13, wherein the abnormal tissue is poorly-differentiated cervical squamous cell carcinoma.

15. The method of claim 1, wherein SUMO-1 colocalization with about 95% of nuclear bodies comprising PML indicates that the abnormal tissue is mild dysplasia, moderate dysplasia, or a combination thereof.

16. The method of claim 1, wherein SUMO-1 colocalization with about 93% of nuclear bodies comprising PML indicates that the abnormal tissue is Type A severe dysplasia.

17. The method of claim 1, wherein SUMO-1 colocalization with about 49% of nuclear bodies comprising PML indicates that the epithelial tissue is abnormal tissue which is Type B severe dysplasia.

18. The method of claim 1, wherein SUMO-1 colocalization of about 18% indicates that the epithelial tissue is abnormal tissue which is well-differentiated cervical squamous cell carcinoma.

19. The method of claim 1, wherein SUMO-1 colocalization of about 10% indicates that the epithelial tissue is abnormal tissue which is poorly-differentiated cervical squamous cell carcinoma.

20. The method of claim 1, wherein the PML expression pattern and SUMO-1 colocalization nuclear bodies comprising PML are fluorescently detected in a paraffin embedded tissue biopsy of the epithelial tissue.

21. A method for diagnosing whether a subject has mild dysplasia, moderate dysplasia, Type A severe dysplasia, Type B severe dysplasia, well differentiated cervical squamous cell carcinoma, or poorly-differentiated cervical squamous cell carcinoma comprising
determining an expression pattern for PML an epithelial tissue sample from the subject;
determining an expression pattern for nuclear bodies in the epithelial tissue sample;
determining a loss of SUMO-1 colocalization with nuclear bodies comprising PML in the epithelial tissue sample; and
determining whether the expression pattern for PML, the expression pattern for nuclear bodies, and the loss of SUMO-1 colocalization with nuclear bodies comprising PML of the epithelial tissue sample is consistent with expression patterns of mild dysplasia, moderate dysplasia, Type A severe dysplasia, Type B severe dysplasia, cervical squamous cell carcinoma, or poorly-differentiated cervical squamous cell carcinoma.

22. The method of claim 21, further comprising determining SUMO-1 colocalization with nuclear bodies comprising PML in the tissue sample, wherein
SUMO-1 colocalization with about 95% of nuclear bodies comprising PML indicates that the subject has mild dysplasia, moderate dysplasia, or a combination thereof;
SUMO-1 colocalization with about 93% of nuclear bodies comprising PML indicates that the subject has Type A severe dysplasia;

SUMO-1 colocalization with about 49% of nuclear bodies comprising PML indicates that the subject has Type B severe dysplasia;

SUMO-1 colocalization with about 18% of nuclear bodies comprising PML indicates that the subject has cervical squamous cell carcinoma; and SUMO-1 colocalization with about 10% of nuclear bodies comprising PML indicates that the subject has poorly-differentiated cervical squamous cell carcinoma.

23. The method of claim 21, wherein
(a) PML expression restricted to the lower half of the epithelium of the epithelial tissue;
(b) nuclear bodies having irregular shapes;
(c) about 9 to about 10 nuclear bodies in the basal layer and upper layer of the epithelial tissue;
(d) nuclear bodies having an area of about 0.52 $\mu m^2$ to about 0.54 $\mu m^2$;
(e) about 95% of the nuclear bodies comprising PML colocalize with SUMO-1; or
(f) a combination thereof indicates that the subject has mild dysplasia, moderate dysplasia, or a combination thereof.

24. The method of claim 21, wherein
(a) PML expression throughout the epithelial tissue;
(b) nuclear bodies which have inconsistent shapes and track like structures;
(c) about 9 to about 10 nuclear bodies in the basal layer and upper layer of the epithelial tissue;
(d) nuclear bodies having an area of about 0.55 $\mu m^2$;
(e) about 93% of the nuclear bodies comprising PML colocalize with SUMO-1; or
(f) a combination thereof indicates that the subject has Type A severe dysplasia.

25. The method of claim 21, wherein
(a) downregulated PML expression;
(b) about 5 nuclear bodies in the basal layer and upper layer of the epithelial tissue;
(c) nuclear bodies having an area of about 0.33 $\mu m^2$;
(d) about 49% of the nuclear bodies comprising PML colocalize with SUMO-1; or
(e) a combination thereof indicates that the subject has Type B severe dysplasia.

26. The method of claim 21, wherein
(a) upregulated PML expression;
(b) variation in the number and size of nuclear bodies;
(c) about 9 nuclear bodies in the epithelial tissue;
(d) nuclear bodies having an area of about 0.73 $\mu m^2$;
(e) about 18% of the nuclear bodies comprising PML colocalize with SUMO-1; or
(f) a combination thereof indicates that the subject has well-differentiated cervical squamous cell carcinoma.

27. The method of claim 21, wherein
(a) downregulated PML expression;
(b) about 5 nuclear bodies in the epithelial tissue; (c) nuclear bodies having an area of about 0.37 $\mu m^2$;
(d) about 10% of the nuclear bodies comprising PML colocalize with SUMO-1; or
(e) a combination thereof indicates that the subject has poorly-differentiated cervical squamous cell carcinoma.

28. The method of claim 21, wherein the subject is mammalian.

29. The method of claim 21, wherein the subject is human.

30. The method of claim 1, wherein the epithelial tissue is cervical epithelial tissue.

31. A method for diagnosing whether a cervical epithelial tissue is an abnormal tissue comprising
determining an expression pattern for PML in the cervical epithelial tissue;
determining an expression pattern for nuclear bodies in the cervical epithelial tissue;
determining a loss of SUMO-1 colocalization with nuclear bodies comprising PML in the cervical epithelial tissue; and
comparing the expression pattern for PML, the expression pattern for nuclear bodies, and the loss of SUMO-1 colocalization with nuclear bodies comprising PML with that of a normal tissue, where loss of SUMO-1 colocalization with nuclear bodies comprising PML indicates abnormal tissue.

\* \* \* \* \*